(12) United States Patent
Kerr et al.

(10) Patent No.: US 9,636,166 B2
(45) Date of Patent: *May 2, 2017

(54) EXTERNAL COOLING DEVICES AND SYSTEMS FOR SURGICAL INSTRUMENTS

(71) Applicant: COVIDIEN LP, Mansfield, MA (US)

(72) Inventors: Duane E. Kerr, Loveland, CO (US); Glenn A. Horner, Boulder, CO (US); Paul Hrenchir, Longmont, CO (US); Peter M. Mueller, Frederick, CO (US); Robert B. Stoddard, Steamboat Springs, CO (US); Luke Waaler, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,773

(22) Filed: Mar. 28, 2016

(65) Prior Publication Data

US 2016/0206365 A1    Jul. 21, 2016

Related U.S. Application Data

(63) Continuation of application No. 14/604,039, filed on Jan. 23, 2015, now Pat. No. 9,301,799, which is a continuation of application No. 13/251,405, filed on Oct. 3, 2011, now Pat. No. 8,945,112.

(51) Int. Cl.
| | | |
|---|---|---|
| *A61B 18/14* | (2006.01) | |
| *A61B 18/12* | (2006.01) | |
| *A61B 90/00* | (2016.01) | |
| *A61B 18/00* | (2006.01) | |
| *A61B 90/50* | (2016.01) | |
| *A61B 17/00* | (2006.01) | |

(52) U.S. Cl.
CPC .......... *A61B 18/14* (2013.01); *A61B 18/1206* (2013.01); *A61B 18/1445* (2013.01); *A61B 90/08* (2016.02); *A61B 90/50* (2016.02); *A61B 2017/00734* (2013.01); *A61B 2018/00023* (2013.01); *A61B 2018/00791* (2013.01); *A61B 2018/1226* (2013.01)

(58) Field of Classification Search
None
See application file for complete search history.

(56) References Cited

U.S. PATENT DOCUMENTS

| | | |
|---|---|---|
| 5,486,162 A | 1/1996 | Brumbach |
| 5,562,609 A | 10/1996 | Brumbach |
| 5,670,860 A | 9/1997 | Conrady et al. |
| 6,588,277 B2 | 7/2003 | Giordano et al. |
| 6,689,087 B2 | 2/2004 | Pal et al. |
| 7,273,483 B2 | 9/2007 | Wiener et al. |
| 7,314,447 B2 | 1/2008 | Park et al. |

(Continued)

*Primary Examiner* — Brian T Gedeon

(57) ABSTRACT

A surgical system includes a portable surgical instrument and a sleeve. The portable surgical instrument includes an end effector assembly and a housing operably coupled to the end effector assembly. The housing includes a generator and a battery assembly coupled thereto and configured to supply energy to the end effector assembly for treating tissue. The sleeve is shaped complementarily to the housing and is removably positionable about the housing. The sleeve is configured to cool the housing and/or remove heat from the housing to inhibit overheating of the generator and/or the battery assembly.

18 Claims, 7 Drawing Sheets

(56) References Cited

U.S. PATENT DOCUMENTS

| | | |
|---|---|---|
| 8,710,407 B2 * | 4/2014 | Heymann .............. A61B 1/128 |
| | | 219/385 |
| 8,932,279 B2 * | 1/2015 | Stringham ........... A61B 18/082 |
| | | 606/29 |
| 8,945,112 B2 | 2/2015 | Kerr et al. |
| 2005/0273126 A1 | 12/2005 | Beaupre |
| 2007/0185554 A1 | 8/2007 | Appling et al. |
| 2009/0131940 A1 | 5/2009 | Brunnett et al. |
| 2009/0171147 A1 | 7/2009 | Lee et al. |

* cited by examiner

EXTERNAL COOLING DEVICES AND SYSTEMS FOR SURGICAL INSTRUMENTS

CROSS-REFERENCE TO RELATED APPLICATIONS

This application is a continuation application of U.S. patent application Ser. No. 14/604,039, filed on Jan. 23, 2015, now U.S. Pat. No. 9,301,799, which is a continuation application of U.S. patent application Ser. No. 13/251,405, filed on Oct. 3, 2011, now U.S. Pat. No. 8,945,112, the entire contents of each of which are hereby incorporated herein by reference.

BACKGROUND

Technical Field

The present disclosure relates to surgical instruments and, more particularly, to external cooling devices and systems for use with portable surgical instruments.

Background of Related Art

Portable surgical instruments are advantageous in that they obviate the need for cables coupling the instrument to an electrical outlet and/or external surgical generator to supply power to the instrument during use. A typical electrosurgical portable instrument generally includes a battery assembly and a generator disposed within or on the instrument itself that, together, cooperate to provide energy to an end effector assembly associated with the instrument. Such portable surgical instruments are more mobile and more easily manipulated within an operating room environment and reduce the number of cables within the operating room, thereby reducing the risk of tripping and/or entanglement. These portable instruments are also enabled for use in non-traditional settings, i.e., outside the operating room environment, where an electrical outlet and/or surgical generator may not be readily available.

However, during the normal course of operation of a portable surgical instrument, the battery and/or the generator (or components associated therewith) may rise in temperature such as, for example, during prolonged periods of use. As can be appreciated, an excessive rise in temperature of the battery and/or the generator may damage the instrument and/or compromise the surgical procedure being performed.

SUMMARY

In accordance with one aspect of the present disclosure, a surgical system including a portable surgical instrument and a sleeve is provided. The portable surgical instrument includes an end effector assembly and a housing operably coupled to the end effector assembly. The housing includes a generator and a battery assembly coupled thereto that are configured to supply energy to the end effector assembly for treating tissue. The sleeve is shaped complementarily to the housing and is removably positionable about the housing. The sleeve is configured to cool the housing and/or remove heat from the housing to inhibit overheating of the generator and/or the battery assembly.

In one aspect, the sleeve includes first and second flaps configured for positioning about either side of the housing. In aspects, the flaps are formed with one another at first ends thereof and are releasably engagable with one another at second ends thereof to secure the sleeve about the housing.

In another aspect, wherein the sleeve includes one or more openings defined therethrough to facilitate operation of the portable surgical instrument with the sleeve disposed about the housing thereof.

In yet another aspect, the sleeve includes one or more internal pockets defined therein. The pocket(s) is configured to retain a coolant member therein for cooling the housing. Alternatively or additionally, the sleeve may be configured to circulate coolant therethrough for cooling the housing.

A surgical system provided in accordance with another aspect of the present disclosure includes a portable surgical instrument and a glove. The portable surgical instrument is similar to the portable surgical instrument of the previous aspect, while the glove is configured to be worn by a user for grasping the housing of the portable surgical instrument. The glove is configured to cool the housing and/or remove heat from the housing to inhibit overheating of the generator and/or the battery assembly.

In aspects, the glove includes one or more lumen extending therethrough. The lumen(s) is configured to permit circulation of a coolant therethrough for cooling the housing. Further, the lumen(s) may be specifically arranged in accordance with the configuration of the portable surgical instrument so as to circulate a relatively greater amount of coolant adjacent the generator and/or the battery assembly. Additionally, a cable may be provided for coupling the fluid lumen(s) to a source of coolant.

In accordance with still another aspect of the present disclosure, a surgical system including a portable surgical instrument and a cannula assembly is provided. The portable surgical instrument includes an end effector assembly, a generator, and a battery assembly, similarly as in the previous aspects. The cannula assembly is configured to permit insertion of the portable surgical instrument therethrough for positioning the end effector assembly within an internal surgical site. Further, the cannula assembly is configured to cool the portable surgical instrument and/or remove heat from the portable surgical instrument to inhibit overheating of the generator and/or the battery assembly.

In one aspect, the cannula assembly includes one or more lumens extending therethrough for circulating coolant therethrough to cooling the portable surgical instrument.

In another aspect, the cannula assembly includes a cannula housing and an elongated tubular member extending from the cannula housing. In such an aspect, the cannula housing includes a coolant member disposed thereon for removing heat from the portable surgical instrument.

In yet another aspect, the cannula assembly includes a proximal extension extending therefrom and configured to extend about a portion of the housing of the portable surgical instrument. The proximal extension is formed (entirely or partially) from a heat-sink material for removing heat from the portable surgical instrument.

A surgical system provided in accordance with still yet another aspect of the present disclosure includes a portable surgical instrument similar to the portable surgical instrument of the previous aspects, and a holster shaped complementarily to the portable surgical instrument. The holster is adapted to receive the portable surgical instrument therein and is configured to cool the portable surgical instrument and/or remove heat from the portable surgical instrument to inhibit overheating of the generator and/or the battery assembly.

In one aspect, the holster includes a barrel portion for receiving the end effector assembly and a first portion of the housing of the portable surgical instrument therein and a base portion for receiving a handle assembly and a second portion of the housing of the portable surgical instrument therein.

The holster may further include a latch member disposed on the outer periphery of the holster for securing the holster in position, e.g., to a belt of the user or on a fixed located within the operating environment.

In accordance with yet another aspect of the present disclosure, a surgical system including a portable surgical instrument and a case is provided. Similar as above, the surgical instrument includes an end effector assembly and a housing operably coupled to the end effector assembly. The housing includes a generator and a battery assembly coupled thereto and configured to supply energy to the end effector assembly for treating tissue. The case is shaped complementarily to the housing and includes first and second components coupled to one another about a hinge. The components are moveable relative to one another about the hinge between an open position, for insertion and removal of the housing from the case, and a closed position, for retaining the housing within the case. Further, the case is configured to cool the housing and/or remove heat from the housing to inhibit overheating of the generator and/or the battery assembly.

In one aspect, one or more releasable engagement members are provided for securing the first and second components in the closed position.

In another aspect, the case is formed (entirely or partially) from a heat-sink material for removing heat from the housing.

BRIEF DESCRIPTION OF THE DRAWINGS

Various aspects of the present disclosure are described hereinbelow with reference to the drawings, wherein.

DETAILED DESCRIPTION

Figure 1A:
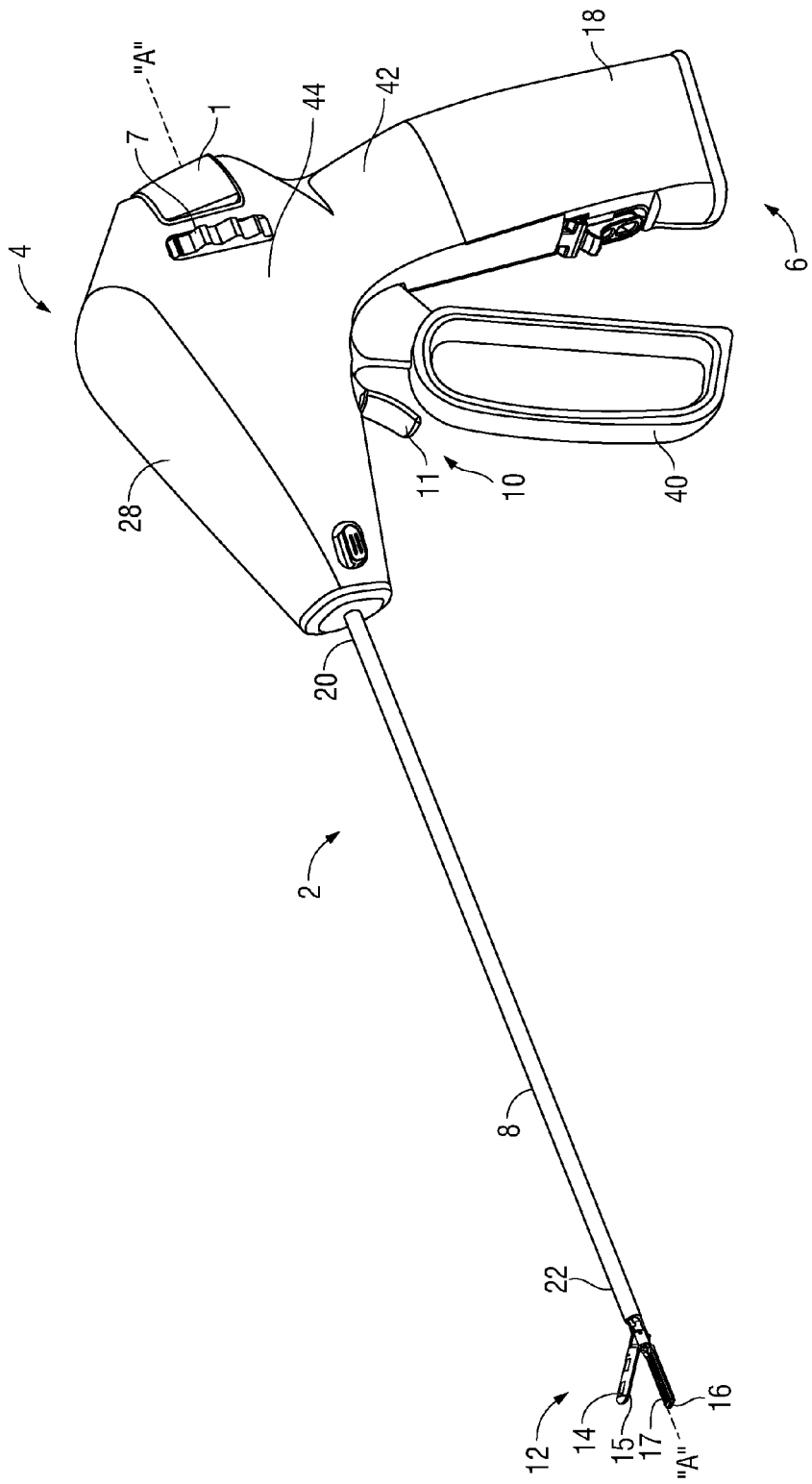
FIG. 1A is a side, perspective view of a portable, battery-powered surgical instrument configured for use in accordance with the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Figure 1B:
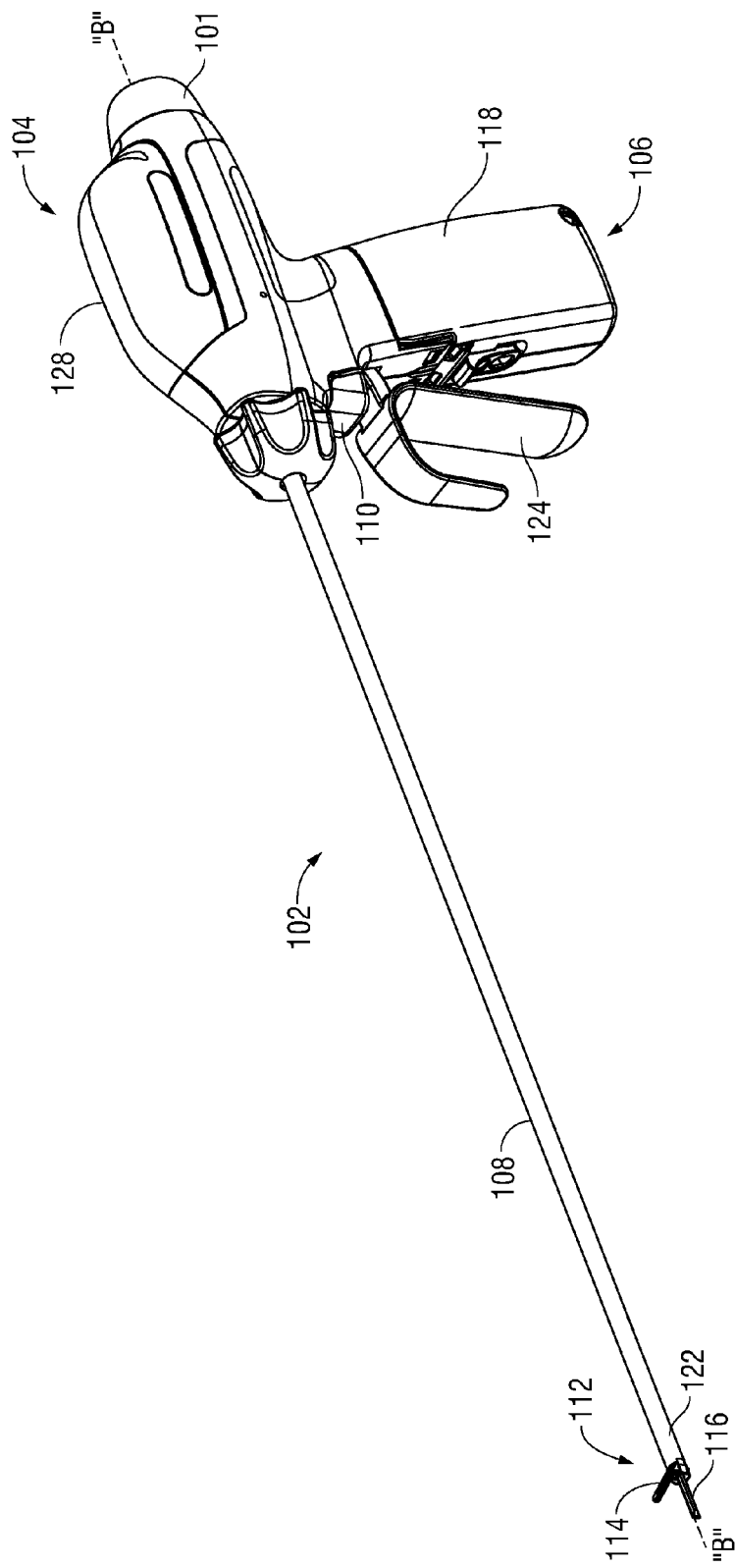
FIG. 1B is a side, perspective view of another portable, battery-powered surgical instrument configured for use in accordance with the present disclosure.

Referring now to FIGS. 1A and 1B, FIG. 1A depicts a portable, battery-powered electrosurgical forceps 2 and FIG. 1B depicts a portable, battery-powered ultrasonic instrument 102. For the purposes herein, either an electrosurgical instrument, e.g., forceps 2, or an ultrasonic instrument, e.g., instrument 102, or any other suitable portable, battery-powered surgical instrument may be utilized in accordance with the present disclosure. Obviously, different considerations apply to each particular type of instrument, however, the novel aspects of the present disclosure are equally applicable to electrosurgical, ultrasonic, and other suitable portable battery-powered surgical instruments.

Electrosurgical forceps 2, as shown in FIG. 1A, generally includes a housing 4, a battery assembly 18, an electrosurgical generator 28, a handle assembly 6, a rotating assembly 7, a shaft 8, a trigger assembly 10, a drive assembly (not shown), and an end effector assembly 12 that operatively connects to the handle assembly 6 via the drive assembly (not shown) for imparting movement of one or both of jaw members 14, 16 of end effector assembly 12 between a spaced-apart, or open position and an approximated, or clamped position for grasping tissue therebetween.

Shaft 8 is coupled to housing 4 at proximal end 20 thereof and extends distally from housing 4 defining longitudinal axis "A-A" therethrough. End effector assembly 12, including jaw members 14 and 16, is disposed at a distal end 22 of shaft 8. Jaw member 14 is movable between a spaced-apart position for positioning tissue between jaw members 14, 16, and an approximated position for grasping tissue between jaw members 14, 16. In other words, end effector assembly 12 is designed as a unilateral assembly, i.e., where jaw member 16 is fixed relative to shaft 8 and jaw member 14 is pivotable relative to jaw member 16 and shaft 8 between the spaced-apart and approximated positions. However, end effector assembly 12 may alternatively be configured as a bilateral assembly, i.e., where both jaw member 14 and jaw member 16 are pivotable relative to one another and to shaft 8.

Forceps 2 may be configured as a bipolar instrument. That is, each of jaw members 14, 16 may include a respective seal plate 15, 17 that is configured to function as an active (or activatable) and/or return electrode. Each seal plate 15, 17 is electrically coupled to generator 28 via one or more electrical leads (not shown) that extend from generator 28, through shaft 8, eventually coupling to one or both of seal plates 15, 17. However, forceps 2 may alternatively be configured as a monopolar instrument.

Handle assembly 6 includes a moveable handle 40 that is movable relative to fixed handle portion 42 for moving jaw members 14, 16 of end effector assembly 12 between the spaced-apart and approximated positions. Rotating assembly 7 rotatable in either direction about longitudinal axis "A-A" to rotate shaft 8 and, thus, end effector assembly 12 about longitudinal axis "A-A." Trigger assembly 10 is in operable communication with a knife assembly (not shown) including a knife blade (not shown) that is selectively translatable between jaw members 14, 16 to cut tissue grasped therebetween, e.g., upon actuation of trigger 11 of trigger assembly 10.

With continued reference to FIG. 1A housing 4 is configured to releasably engage electrosurgical generator 28 and battery assembly 18 therein. Generator 28 is releasably engagable with body portion 44 of housing 4, while battery assembly 18 is releasably engagable with fixed handle portion 42 of housing 4. More specifically, battery assembly 18 is configured to engage fixed handle portion 42 of housing 4 and such that battery assembly 18 functions as a stationary handle and provides a gripping surface for the user. Generator 28 releasably engages body portion 44 of housing 4 and may be selectively removable therefrom either in connection with removal of battery assembly 18 or independently thereof. When forceps 2 is assembled, generator 28 is disposed in operable communication with battery assembly 18 to provide electrosurgical energy at one or more suitable frequencies to end effector 12 for electrosurgically treating tissue, e.g., to seal tissue. In particular, generator 28 may include electronics that convert the electrical energy from battery assembly 18 into an RF energy waveform to energize one or both of jaw members 14, 16. That is, generator 28 may be configured to transmit RF energy to seal plate 15 of jaw member 14 and/or seal plate 17 of jaw member 16 to seal tissue. Activation switch 1 disposed on housing 4 is activatable for selectively enabling generator 28 to generate and, subsequently, transmit RF energy to seal plate 15 and/or seal plate 17 of jaw members 14, 16, respectively.

Referring now to FIG. 1B, ultrasonic instrument 102 includes components similar to that of forceps 2 (FIG. 1A), namely, a housing 104, a battery assembly 118, a generator 128, a handle assembly 106, a shaft 108, and an end effector assembly 112. Accordingly, only the difference between ultrasonic instrument 102 and bipolar forceps 2 (FIG. 1A) will be described hereinbelow for purposes of brevity.

Housing 104 is configured to releasably engage ultrasonic generator 128 and battery assembly 118 thereon or therein. Shaft 108 extends distally from housing 104 defining longitudinal axis "B-B" and includes end effector assembly 112 disposed at distal end 122 thereof. One or both of jaw members 114 and 116 of end effector assembly 112 are movable relative to one another, upon actuation of moveable handle 124, between an open position and a clamping position for grasping tissue therebetween. Further, one of the jaw members, e.g., jaw member 116 serves as an active or oscillating ultrasonic blade that is selectively activatable to seal tissue grasped between jaw members 114, 116.

Generator 128 includes a transducer (not shown) configured to convert electrical energy provided by battery assembly 118 into mechanical energy that produces motion at the end of a waveguide, e.g., at blade 116. More specifically, the electronics (not explicitly shown) of the generator 128 convert the electrical energy provided by battery assembly 118 into a high voltage AC waveform that drives the transducer (not shown). When the transducer (not shown) and the waveguide are driven at their resonant frequency, mechanical, or ultrasonic motion is produced at the active jaw member 116 for sealing tissue grasped between jaw members 114, 116. Further, an activation button 110 disposed on housing 104 is selectively activatable to operate instrument 102 in two modes of operation: a low-power mode of operation and a high-power mode of operation.

As can be appreciated, during the normal course of operation of forceps 2 (FIG. 1A), ultrasonic instrument 102 (FIG. 1B), and other portable, battery-powered instruments, the battery assembly 18, 118 and/or generator 28, 128 (or components associated therewith) may rise in temperature, particularly during repeated use or periods of prolonged use. Accordingly, various embodiments of external cooling devices and systems provided in accordance with the present disclosure are described hereinbelow. These external cooling devices and systems are configured to function as heat sinks, either actively or passively, to remove heat from battery assembly 18, 118 and/or generator 28, 128 of instruments 2, 102, respectively, and/or to actively cool battery assembly 18, 118 and/or generator 28, 128 of instruments 2, 102, respectively, thereby helping to maintain instruments 2, 102 at a safe operating temperature. The external cooling devices and systems described herein may be adapted for use in conjunction with forceps 2 (FIG. 1A), ultrasonic instrument 102 (FIG. 1B), or any other portable, battery-powered instrument. However, for purposes of simplicity and consistency, each of the exemplary embodiments will be described hereinbelow with reference to forceps 2 only. Further, any of the features described with respect to any of the embodiments below may similarly be configured for use in conjunction with any of the other embodiments described herein.

Figure 2:
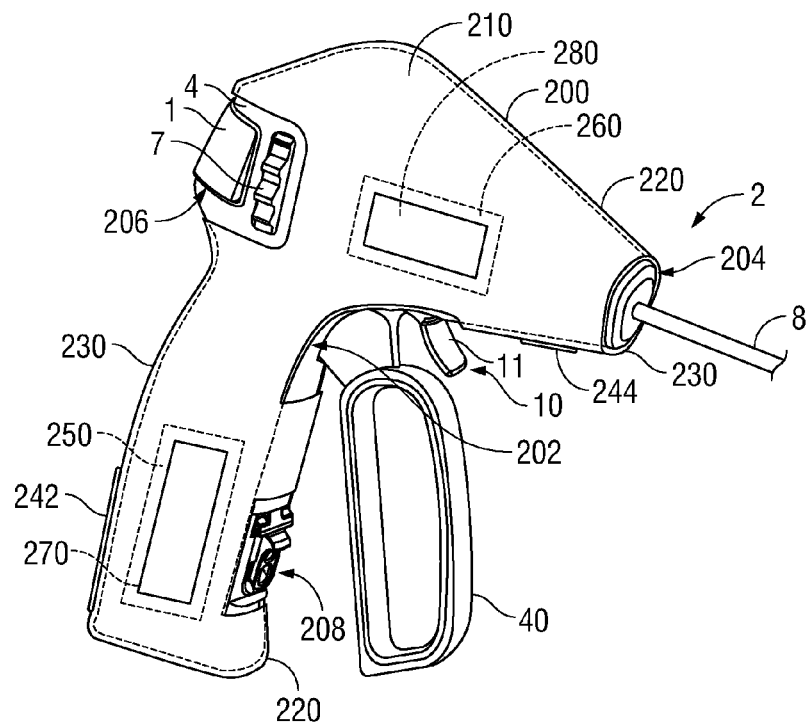
FIG. 2 is a side, perspective view of a housing of the instrument of FIG. 1A including a cooling sleeve disposed thereabout.

Turning now to FIG. 2, one embodiment of a cooling device, or heat sink configured for use with forceps 2 is shown generally identified as sleeve 200. Sleeve 200 is removably positionable about housing 4 of forceps 2 and is configured to remove heat from and/or cool housing 4 of forceps 2, thereby inhibiting overheating of battery assembly 18 and/or generator 28 (see FIG. 1A).

As shown in FIG. 2, sleeve 200 is configured to substantially surround housing 4 and defines a complementary configuration to housing 4 to facilitate positioning of sleeve 200 thereabout. Further, sleeve 200 includes a handle and trigger opening 202, a shaft opening 204, and an activation switch and rotation assembly opening 206. Handle and trigger opening 202 permits extension of movable handle 40 and trigger 11 of trigger assembly 10 from sleeve 200 such that movable handle 40 and trigger 11 may be manipulated by the user; shaft opening 204 permits extension of shaft 8 from housing 4; and activation switch and rotation assembly opening 206 provides access to activation switch 1 for selectively activating forceps 10 as well as access to rotation assembly 7 for rotating end effector assembly 12 (FIG. 1A) about longitudinal axis "A-A" (FIG. 1A). In other words, openings 202, 204, 206 permit full operation and use of forceps 20 when sleeve 200 is disposed thereabout. Other openings, e.g., battery control opening 208, may also be provided, depending on the particular configuration of the surgical instrument to be used. As such, although sleeve 200 is shown configured for use with forceps 2, sleeve 200 may alternatively be configured for use with any other suitable surgical instrument, e.g., instrument 102 (FIG. 1B).

With continued reference to FIG. 2, sleeve 200 is of unitary construction (although other configurations are contemplated) and includes a first flap 210 configured for positioning about one side of housing 4 and a second flap (not shown), similar to first flap 210, that is configured for positioning about the other side of housing 4. First flap 210 and the second flap (not shown) are formed with one another at first ends 220 thereof and are releasably engagable with one another at various positions along second ends 230 thereof, e.g., via releasable engagement members 242, 244. Releasable engagement members 242, 244 may include VELCRO™, snaps, buttons, etc., or any other suitable releasable engagement mechanisms. As such, in order to position sleeve 200 about housing 4 of forceps 2, housing 4 is positioned between first flap 210 and the second flap (not shown) of sleeve 200 and first flap 210 and the second flap (not shown) are wrapped about housing 4, ultimately engaging one another at second ends 230 thereof for securing sleeve 200 about housing 4 of forceps 2.

Sleeve 200 may further include internal pockets 250, 260 configured to retain coolant members 270, 280, respectively, e.g., chemical coolant pouches, fluid coolant pouches, heat sinks (passive or active), thermal pads, conductive materials, coolant materials, etc., therein for removing heat from and/or cooling housing 4. These coolant members 270, 280 may be removed from pockets 250, 260 and interchanged with different coolant members to achieve a desired configuration or effect, e.g., depending on the cooling needs of the particular surgical instrument used in conjunction with sleeve 200. Sleeve 200 may also include sensors (not shown) or other monitoring devices for monitoring the external temperature of housing 4 at various positions thereon, e.g., adjacent battery assembly 18 and adjacent generator 28 (see FIG. 1A).

Alternatively or additionally, sleeve 200 may include fluid lumens (not shown), e.g., fluid lumens similar to fluid lumens 310 of glove 300 (see FIG. 3), extending therethrough that are configured to permit circulation of coolant therethrough for cooling battery assembly 18 and generator 28 (see FIG. 1A) of housing 4 of forceps 2. Further, sleeve 200 may itself be formed at least partially from conductive materials so as to act as a heat sink for transferring heat away from battery assembly 18 and generator 28 (see FIG. 1A), thereby inhibiting overheating of housing 4 and/or the components thereof.

Figure 3:
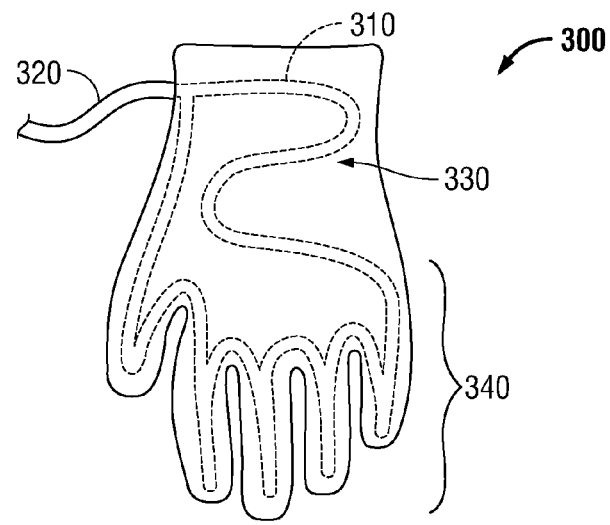
FIG. 3 is a top view of a cooling glove configured for use with the instruments of FIG. 1A and FIG. 1B.

Referring now to FIG. 3, in conjunction with FIG. 1A, a glove configured for use with forceps 2, or any other suitable surgical instrument, is shown generally identified by reference numeral 300. Glove 300 is configured to be worn by the user on the hand that is to grasp forceps 2 for removing heat from and/or cooling housing 4 of forceps 2. Glove 300 is formed from a sufficiently flexible material and is sufficiently thin so as to not substantially inhibit the user's dexterity, thus allowing the user to properly control and manipulate forceps 2 as desired. Glove 300 further includes one or more fluid lumens 310 extending therethrough. Fluid lumens 310 are ultimately coupled to a coolant source (not shown) via cable 320 to permit circulation of coolant through glove 300 in order to cool battery assembly 18 and generator 28 of housing 4 of forceps 2 during use. Alternatively, or additionally, glove 300 may be formed at least partially from a heat sink or conductive material, or may include other coolant members or heat-sinks, e.g., chemical coolant pouches, fluid coolant pouches, heat sinks (passive or active), thermal pads, conductive materials, coolant materials, etc., disposed therein for removing heat from and/or cooling housing 4 during use of forceps 2. In embodiments where active heat sinks are provided, a cable (not shown) may be used to power the active heat sink (not shown) disposed within glove 300.

The particular configuration of fluid lumens 310 of glove 300 (or the other coolant members used therewith) may depend on the configuration of the surgical instrument to be used. For example, glove 300 may include a greater concentration of fluid lumens 310 in the vicinity of palm section 330 thereof since the user typically palms fixed handle 42 and battery assembly 18 of housing 4 in order to grasp forceps 2. Thus, a relatively higher amount of coolant will be circulated about battery assembly 18 to help maintain battery assembly 18 within an acceptable temperature range. Similarly, in embodiments where the user is to grasp battery assembly 18, generator 28, or components thereof with the user's fingers, the finger portion 340 of glove 300 may include an increased concentration of fluid lumens 310 extending therethrough. As can be appreciated, glove 300 may define any other suitable configuration for providing an increased concentration of coolant circulation adjacent battery assembly 18, generator 28, or another component of housing 4. Glove 300 may likewise include sensors (not shown) or other monitoring devices, similarly as descried above with respect to sleeve 200 (FIG. 2).

Figure 4:
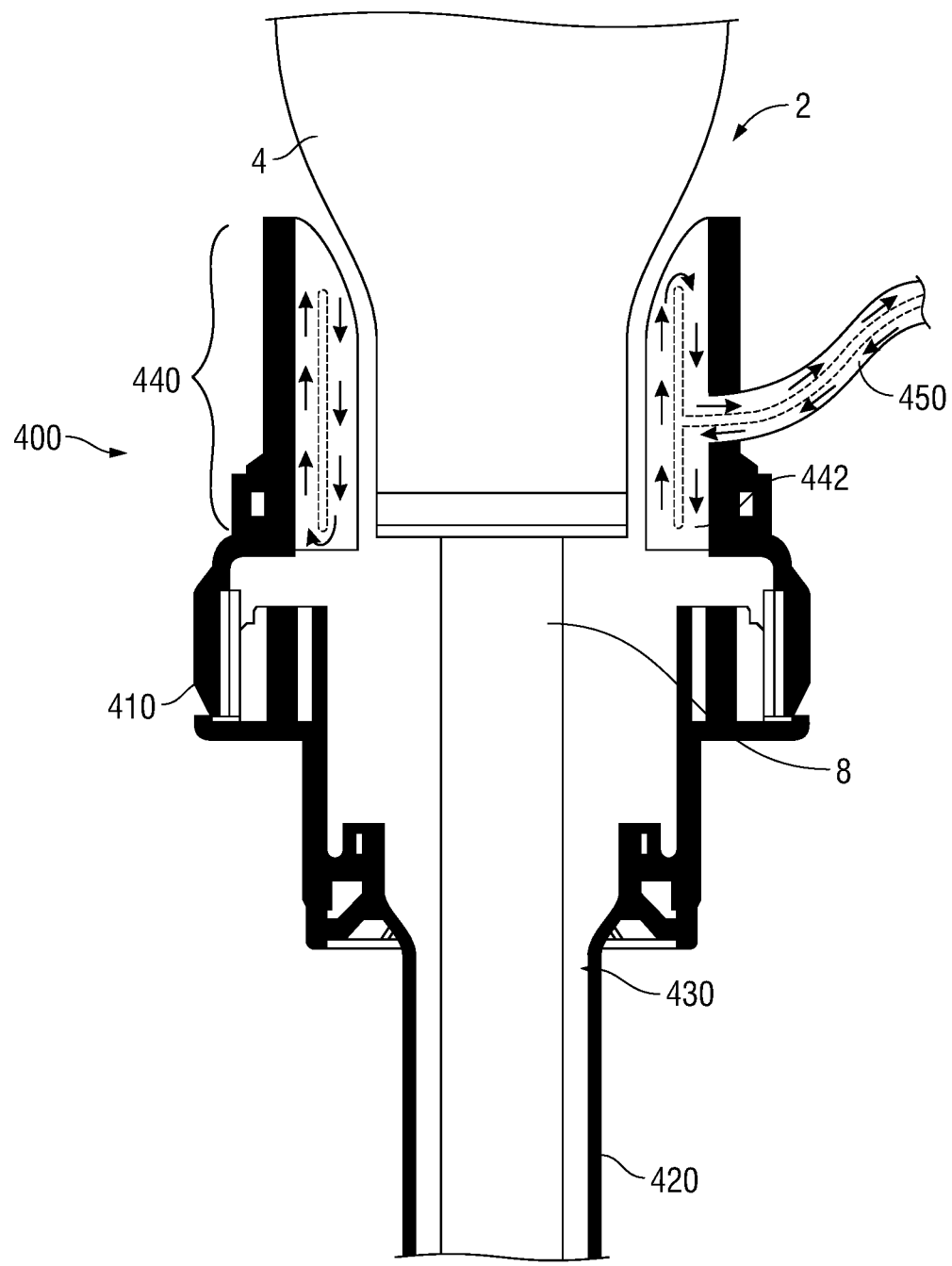
FIG. 4 is a longitudinal, cross-sectional view of the instrument of FIG. 1A inserted through a cooling cannula assembly.

With reference to FIG. 4, a cannula assembly 400 configured for use in conjunction with forceps 2 during the course of minimally-invasive surgical procedures is shown. Cannula assembly 400 generally includes a cannula housing 410 and an elongated tubular member 420 extending distally from cannula housing 410. Cannula housing 410 and elongated tubular member 420 cooperate to define a longitudinal passage 430 extending therethrough that is configured to permit insertion of end effector assembly 12 (FIG. 1A) and shaft 8 of forceps 2 therethrough for positioning end effector assembly 12 (FIG. 1A) adjacent an internal surgical site. Cannula housing 410 further includes a proximal extension 440 releasably coupled thereto, or formed therewith, that is configured to remove heat from and/or cool forceps 2 during use. More specifically, proximal extension 440 includes an annular lumen 442 that is disposed about at least a portion of housing 4 of forceps 2 and is configured to permit circulation of a coolant therethrough for cooling the outer periphery of shaft 8 and/or housing 4 of forceps 2. Coolant may be provided from a coolant source (not shown) via cable 450. Alternatively, proximal extension 440 may be formed at least partially from a heat sink or conductive material, or may include other coolant members or heat-sinks (such as those discussed above) for removing heat from and/or cooling forceps 2 during use.

Figure 5:
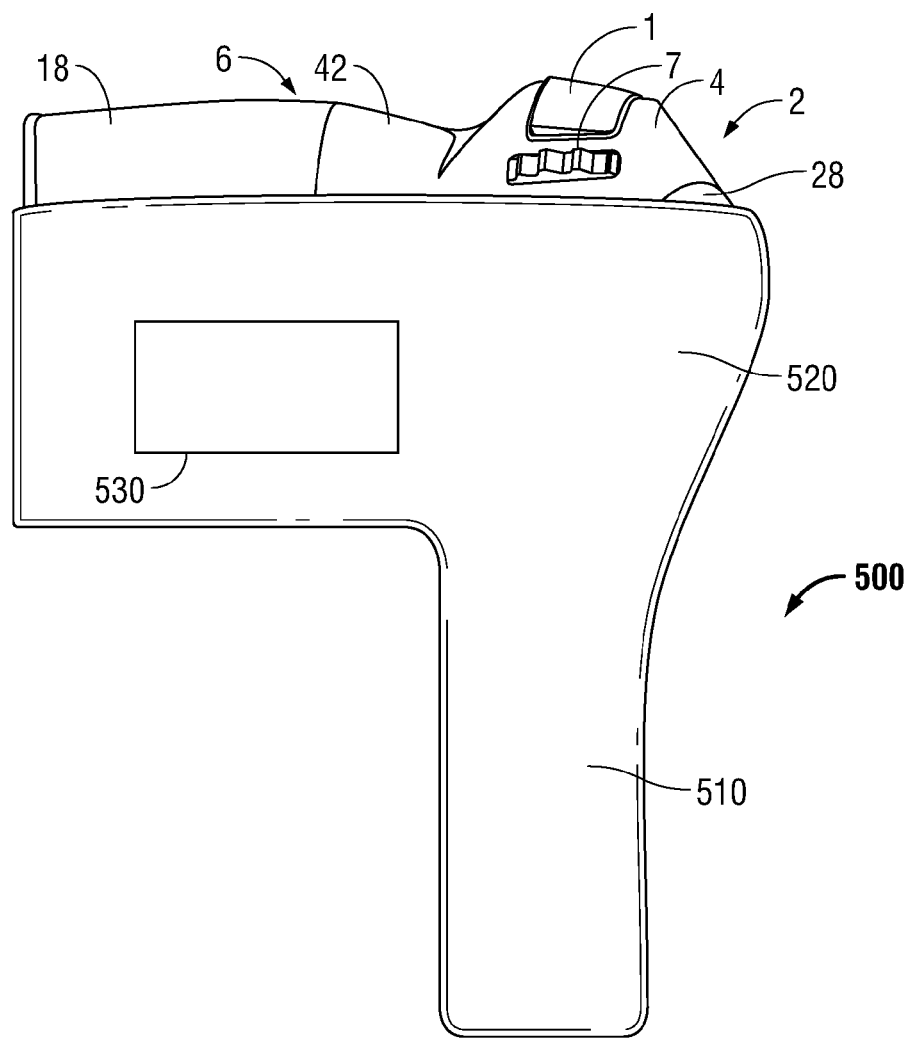
FIG. 5 is a side view of the instrument of FIG. 1A disposed within a cooling holster.

FIG. 5 depicts another embodiment of a cooling device, holster 500, configured for use with forceps 2, or any other suitable instrument, for removing heat from and/or cooling forceps 2. However, rather than cooling forceps 2 during use, holster 500 is configured to retain forceps 2 therein when forceps 2 is not in use, thus ensuring that forceps 2 is maintained, or returned to an acceptable temperature for subsequent use.

Holster 500 generally includes an elongated barrel portion 510 configured to receive end effector assembly 12 (FIG. 1A), shaft 8 (FIG. 1A), and the distal portion of housing 4 and generator 28 therein, and a base portion 520 that is configured to receive the proximal portion of housing 4 and generator 28, as well handle assembly 6 and battery assembly 18 therein. Although one configuration of holster 500 is shown for use with forceps 2, holster 500 may alternatively be configured complementary to any other surgical instrument configured for use therewith, or may be universally configured to receive various different surgical instruments therein. Further, holster 500 may incorporate any of the cooling, or heat sink mechanisms discussed above with respect to sleeve 200 (FIG. 2), glove 300 (FIG. 3) and/or cannula assembly 400 (FIG. 4), or any other suitable cooling or heat sink mechanism. For example, holster 500 may be formed from a heat sink, or conductive material so as to draw heat away from forceps 2, thus facilitating the cooling of forceps 2 between uses.

Holster 500 may further include a latch member 530, or other suitable securement member, disposed on the outer periphery thereof for releasably engaging holster 500 to the user's belt, or any suitable fixture within the operating environment so as to conveniently position holster 500 as desired to facilitate repeated insertion and removal of forceps 2 from holster 500 during the course of a surgical procedure.

Figure 6:
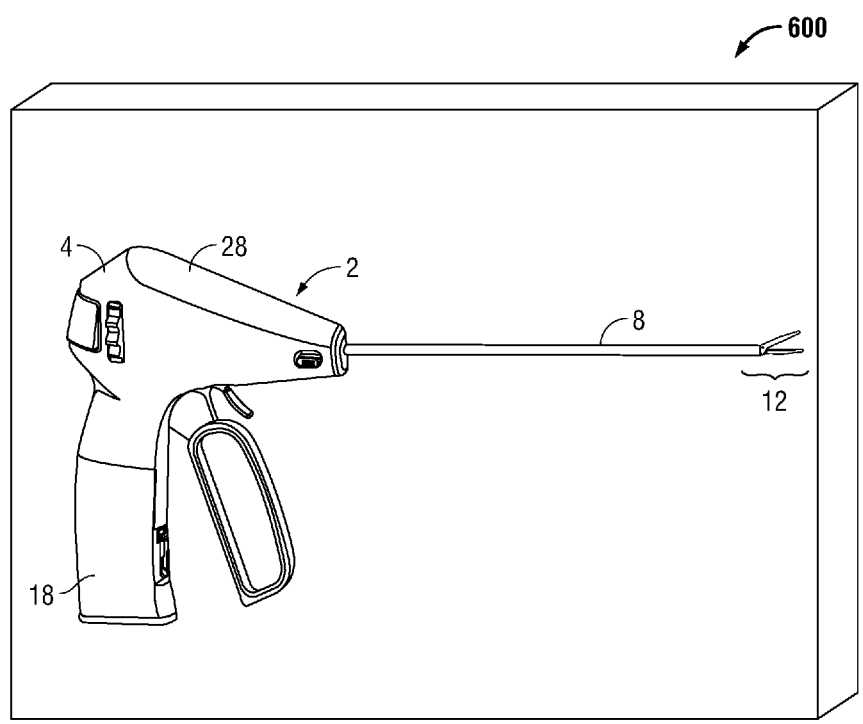
FIG. 6 is a top view of the instrument of FIG. 1A positioned on a cooling plate.

Referring now to FIG. 6, a cooling plate 600 is shown configured for use with forceps 2 or any other suitable surgical instrument. Similar to holster 500 (FIG. 5), cooling plate 600 is configured to receive forceps 2 thereon when forceps 2 is not in use, thus ensuring that forceps 2 is maintained, or returned to an acceptable temperature for subsequent use. Cooling plate 600 may incorporate any of the cooling, or heat sink mechanisms discussed above with respect to the previous embodiments. For example, cooling plate 600 may be formed from a natural heat sink material such as a dense stone, e.g., marble, metal, e.g., aluminum or copper, or other suitable material.

Figure 7:
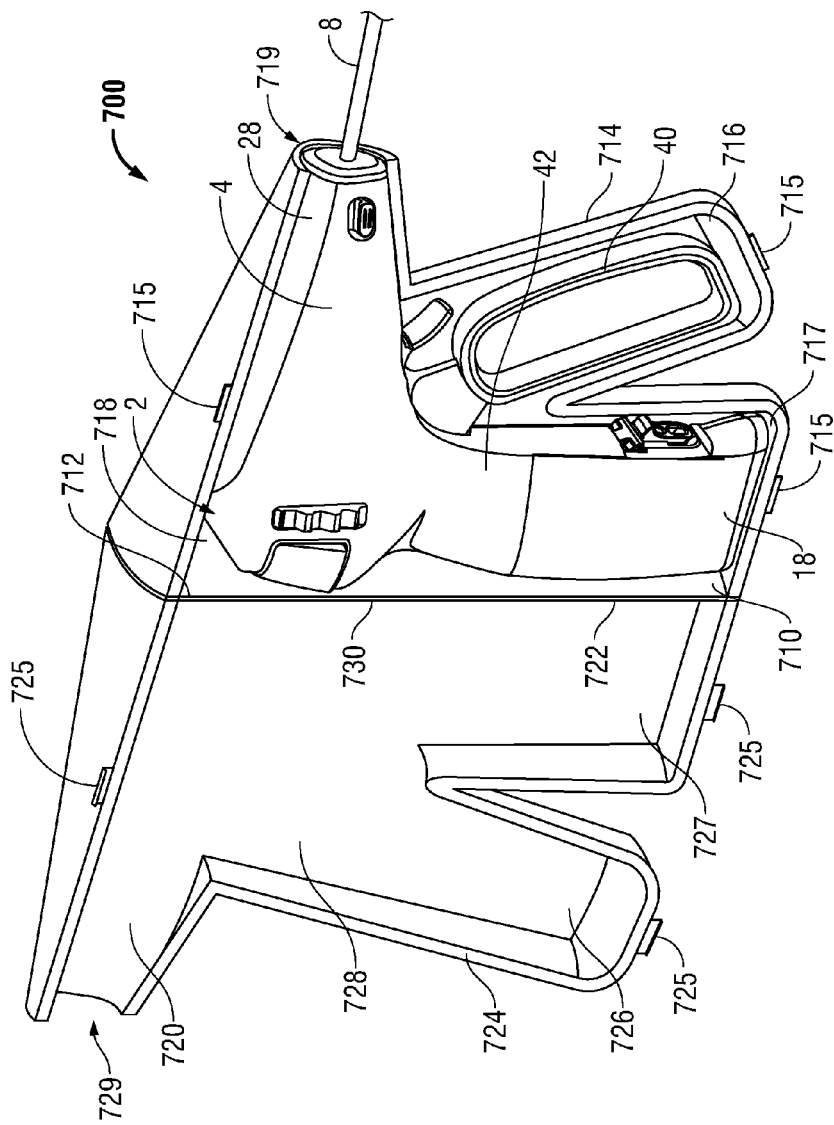
FIG. 7 is a top view of the instrument of FIG. 1A disposed within a cooling case.

Turning now to FIG. 7, case 700 is configured for receiving forceps 20 therein in order to remove heat from and/or cool housing 4 of forceps 2 when forceps 2 is not in use, thus ensuring that forceps 2 is maintained, or returned to an acceptable temperature for subsequent use. As such, case 700 may incorporate any of the cooling, or heat sink mechanisms discussed above with respect to the previous embodiments, or any other suitable cooling, or heat sink mechanism for removing heat from and/or cooling forceps 2.

Case 700 generally includes a first case half 710 configured for positioning about one side of housing 4 and a second case half 720, similar to first case half 710, that is configured for positioning about the other side of housing 4. First and second case halves 710, 720, respectively, are pivotably engaged to one another via hinge 730 at first ends 712, 722, respectively, thereof and are releasably engagable with one another at various positions along second ends 714, 724, respectively, thereof via complementary releasable engagement members 715, 725, respectively. Releasable engagement members 715, 725 may include latches, snaps, buttons, etc., or any other suitable releasable engagement mechanisms for engaging first and second case halves 710, 720 to one another to enclose and retain forceps 2 therein. As can be appreciated, this configuration permits first and second case halves 710, 720, respectively, to move relative to one another between an open position, for insertion and removal of forceps 2 therefrom, and a closed, or locked position for securing forceps 2 therein.

Continuing with reference to FIG. 7, case 700, as mentioned above, is configured for use with forceps 2 and defines a complementary configuration with respect to forceps 2. More specifically, case halves 710, 720 of case 700 each include a movable handle retaining portion 716, 726 configured to receive moveable handle 40 therein, a fixed handle and battery assembly portion 717, 727, configured to receive fixed handle 42 and battery assembly 18 therein, and a housing and generator portion 718, 728 configured to receive housing 4 and generator 28 therein. An aperture 719, 729 is also defined therethrough to permit extension of shaft 8 of forceps 2 therefrom, although case 700 may alternatively be configured to receive shaft 8 and end effector assembly 12 (FIG. 1A) within a shaft receive portion (not shown) thereof. This configuration, wherein case 700 is shaped complementary to forceps 2, maximizes the surface area contact between forceps 2 and case 700, thus facilitating heat removal and/or cooling of forceps 2. Thus, as can be appreciated, although case 700 is shown configured for use with forceps 2, case 700 may alternatively be configured for use with any other suitable surgical instrument to achieve the same purpose.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
   a surgical instrument including a housing having a handle configured to be grasped by a user, a shaft extending distally from the housing, and an end effector extending distally from the shaft, wherein at least one component supported on or within the housing produces heat during use of the surgical instrument; and
   a cooling device configured to removably receive at least a portion of the housing of the surgical instrument when the surgical instrument is not in use, the surgical instrument configured for removal from the cooling device for use of the surgical instrument, the cooling device configured to actively cool the at least one component when the surgical instrument is received by the cooling device.

2. The surgical system according to claim 1, wherein the cooling device is configured to actively cool the at least one component of the surgical instrument by circulating a fluid through the cooling device.

3. The surgical system according to claim 2, wherein the cooling device defines at least one lumen extending therethrough, the at least one lumen configured to permit circulation of the fluid therethrough.

4. The surgical system according to claim 3, further comprising a cable coupling the at least one lumen to a source of fluid.

5. The surgical system according to claim 1, wherein the cooling device includes an active heat sink configured to actively cool the at least one component of the surgical instrument.

6. The surgical system according to claim 1, wherein the cooling device includes a cooling plate defining a surface configured to receive the surgical instrument thereon when the surgical instrument is not in use.

7. The surgical system according to claim 1, wherein the cooling device includes a holster defining an interior configured to receive at least a portion of the surgical instrument therein when the surgical instrument is not in use.

8. The surgical system according to claim 1, wherein the cooling device includes a case configured to receive and enclose the surgical instrument therein when the surgical instrument is not in use.

9. The surgical system according to claim 1, wherein the cooling device further includes at least one sensor configured to sense a temperature of at least a portion of the surgical instrument.

10. The surgical system according to claim 1, wherein the at least one component includes a battery and a generator, the battery configured to power the generator and the generator configured to supply energy to the end effector, wherein the battery and generator produce heat during use of the surgical instrument.

11. The surgical system according to claim 1, wherein the end effector of the surgical instrument is configured to supply RF energy to tissue to treat tissue during use of the surgical instrument.

12. The surgical system according to claim 1, wherein the end effector of the surgical instrument is configured to supply ultrasonic energy to tissue to treat tissue during use of the surgical instrument.

13. A method of surgery, comprising:
   using a surgical instrument a first time, wherein using the surgical instrument the first time includes treating tissue with an end effector extending distally from a shaft, the shaft having a housing including a handle configured to be grasped by a user, the housing extending proximally from the shaft, wherein at least one component supported on or within the housing produces heat during the use of the surgical instrument;

placing the surgical instrument such that at least a portion of the housing is removably received by a cooling device;

actively cooling the at least one component of the surgical instrument using the cooling device;

removing the at least a portion of the housing from the cooling device; and using the surgical instrument a second time, wherein using the surgical instrument the second time includes treating tissue with the end effector.

14. The method according to claim 13, wherein using the surgical instrument at least one of the first or second times includes treating tissue with RF energy.

15. The method according to claim 13, wherein using the surgical instrument at least one of the first or second times includes treating tissue with ultrasonic energy.

16. The method according to claim 13, wherein actively cooling the at least one component using the cooling device includes circulating fluid through the cooling device.

17. The method according to claim 13, wherein actively cooling the at least one component using the cooling device includes activating an active heat sink.

18. The method according to claim 13, further comprising sensing a temperature of at least a portion of the surgical instrument when the at least a portion of the housing is removably received by the cooling device.

* * * * *